United States Patent [19]

Brandt

[11] Patent Number: 4,931,632

[45] Date of Patent: Jun. 5, 1990

[54] VARIABLE PARAMETER OPTICAL BOTTLE CHECKER

[75] Inventor: Thomas L. Brandt, Windsor, N.Y.

[73] Assignee: Brandt Manufacturing Systems, Inc., Deposit, N.Y.

[21] Appl. No.: 254,640

[22] Filed: Oct. 7, 1988

[51] Int. Cl.⁵ .............................................. G01N 9/04
[52] U.S. Cl. .................................. 250/223 B; 356/240
[58] Field of Search ................. 250/223 B; 209/523, 209/524, 526, 538; 356/239, 240

[56] References Cited

U.S. PATENT DOCUMENTS

| | | | |
|---|---|---|---|
| 3,557,950 | 1/1971 | Powers | 250/223 B |
| 3,690,456 | 9/1972 | Powers | 209/526 |
| 3,880,750 | 4/1975 | Butler et al. | 250/223 B |
| 4,213,702 | 7/1980 | Bryant et al. | 250/223 B |
| 4,454,542 | 6/1984 | Miyazawa | 209/526 |
| 4,467,350 | 8/1984 | Miller | 250/223 B |
| 4,488,648 | 12/1984 | Claypool | 250/223 B |
| 4,509,075 | 4/1985 | Simms et al. | 250/223 B |
| 4,584,469 | 4/1986 | Lovalenti | 250/223 B |
| 4,601,395 | 7/1986 | Juvinall et al. | 250/223 B |
| 4,764,681 | 8/1988 | Michalski et al. | 250/223 B |

Primary Examiner—David C. Nelms
Assistant Examiner—Stephone B. Allen
Attorney, Agent, or Firm—Sughrue, Mion, Zinn, Macpeak & Seas

[57] ABSTRACT

A computerized bottle checker which detects the reflection or transmission of light from a rotating bottle to be checked for flaws. A bottle is rejected if the light exceeds a predetermined threshold level for a time period falling between a minimum and a maximum time. The threshold level can be automatically determined by testing a standard bottle with a known flaw and setting the threshold level to a constant fraction of the peak level for a complete rotation of the bottle. The minimum and maximum times can be set to constant fractions of the time period for which the light from the standard bottle exceeds the threshold.

15 Claims, 9 Drawing Sheets

VARIABLE PARAMETER OPTICAL BOTTLE CHECKER

BACKGROUND OF THE INVENTION

1. Field of the Invention

The invention relates generally to optical bottle checkers. In particular, the invention relates to a programmable, automatic optical bottle checker.

2. Background Art

Figures 1, 2:
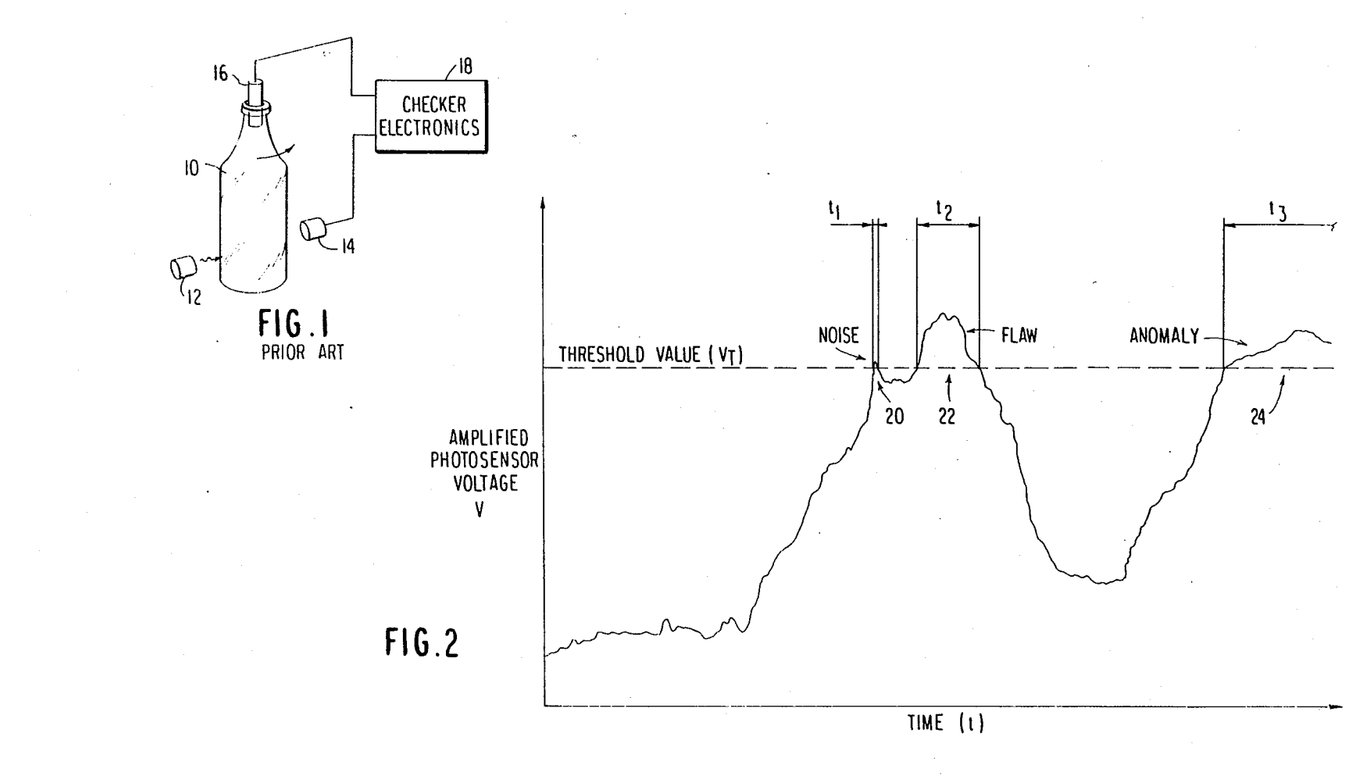
FIG. 1 is a schematic illustration of the principle of operation of an optical bottle checker.
FIG. 2 is a signal vs. time profile for an optical signal from a production bottle.

There are many well known devices for checking for flaws or defects in glass containers, hereafter simply called bottles. One type of bottle checker is disclosed by Powers in U.S. Pat. No. 3,557,950. Improvements of this bottle checker are disclosed by Powers in U.S. Pat. No. 3,690,456 and by Bryant et al in U.S. Pat. No. 4,213,702. The mechanics of this system are briefly summarized here. Bottles are conveyed along a conveyor line past a checking station. At the checking station, a carriage moves reciprocally along the conveyor line in synchronism with the bottles. The carriage grasps the bottle and then rotates it. As schematically illustrated in FIG. 1, as a bottle 10 is being rotated by the moving carriage several light sources 12 (only one is here illustrated) shine light toward the bottle 10. At least one light sensor 14 is carried by the carriage and is positioned at the side of the rotating bottle 10, and other light sensors may be provided. A probe 16 may be inserted into the neck of the bottle 10 to check for flaws on the bottle lip. The level of each photosensor output is proportional to the light transmitted through the bottle to that photosensor, or alternatively to the amount of light reflected from the bottle to that photosensor. The outputs of the various light sensors are supplied to a checker electronics system. If there are flaws in the bottle 10, then the flaws cause uneven reflection or transmission of light as the bottle is rotated. Powers '950 checks to determine if the light level is above a threshold value, whereas Bryant et al '702 checks to determine if the difference between the outputs of two sensors at spaced apart locations exceeds a threshold. The checker electronics system 18 then determines that an unacceptable flaw is present in the bottle 10 and rejects that bottle.

Although an embodiment of the checker electronics system 18 is disclosed in the first Powers patent, an improved electronics system usable with the Powers bottle checker is disclosed by Claypool in U.S. Pat. No. 4,488,648. The two Powers patents and the the Claypool U.S. Pat. No. are incorporated herein by reference. A bottle checking system implementing these three patents is available from Powers Manufacturing. Inc. of Elmira. N.Y.

The Claypool electronics system is controlled by a microcomputer. The sensor outputs are sampled 416 times for a 405° rotation of the bottle, and the samples are digitized and stored in a data memory. The electronics then compares the digitized data and, if there is a difference therebetween which is greater than a set threshold, the bottle is rejected. In the disclosed system, the data memory contains four data samples with the oldest and newest samples being compared. The difference between compared samples, analogous to the slope of the change in the photosensor output, is then compared to a manually set threshold level.

One of the drawbacks of the Claypool system is that the threshold value needs to be programmed into the electronics system based upon whether the system rejects bottles having known flaws. That is, the set up is by trial and error. Both a "good" bottle and a flawed bottle are passed through the system with continual adjustments of the threshold value until the good bottle is passed and the flawed bottle is rejected. This process needs to be repeated for each photosensor and for each different type of flaw. If the bottle checker is used on a production line changing between different types of bottles, the complexity of the set-up causes production inefficiencies.

Furthermore, the slope comparison method of Claypool suffers from the disadvantage that the slope is dependent upon the speed of rotation of the bottle. Thus, if the bottle production rate is changed, the threshold needs to be changed if anomalies and flaws are to be consistently distinguished. Similarly, for a small diameter container, a much lower threshold is required than for large diameter containers.

Another drawback of the Claypool system, is that the reject criterion is a simple comparison of the slope of the light signal against a threshold. Although there are other prior art bottle checkers which reject a bottle only when the light interruption persists for a threshold duration, it is felt that the reject criterion is still too simple to adequately reject known types of flaws while accepting other aberrations in the bottle which are not true defects.

Yet further, there is a need for faster analog-todigital conversion in converting the outputs of the photosensors to a form usable in digital processing in the checker electronics. There is also a need for a wider range of amplification gain for the photosensor outputs.

SUMMARY OF THE INVENTION

Accordingly, an object of the invention is to provide an optical bottle checker which can be set up automatically for different types of bottles.

Another object of the invention is to provide an optical bottle checker which can more reliably detect flaws without rejecting acceptable bottles.

The invention can be summarized as an optical checker for detecting flaws in a container such as a glass bottle. The container is rotated while being illuminated with a beam of light. A sensor detects fluctuations in the light which would be caused by flaws. According to the invention, a flaw is determined when the detected light intensity exceeds a predetermined threshold for a length of time falling between a minimum duration and a maximum duration. Also, according to the invention, the parameters of the checker can be automatically programmed by passing a container with a known flaw through the checker and setting the parameters according to preset equations dependent upon the detected light waveform.

DETAILED DESCRIPTION OF THE PREFERRED EMBODIMENT

The present invention is a computerized optical bottle checker which rejects a bottle when an optical signal exceeds a threshold $V_T$ for a length of time between a minimum duration $T_{min}$ and a maximum duration $T_{max}$. A typical profile of the signal voltage vs. degree of rotation of the bottle (which is operationally proportional to time) is shown in FIG. 2. There are three types of peaks which exceed the threshold. A noise peak 20 has a relatively short duration $t_1$. In any production environment, electronic and optical noise are unavoidable. A flaw peak 22 has an intermediate duration $t_2$. An anomaly peak 24 has a relatively long duration $t_3$. Such anomalies are discussed in the Claypool patent and arise from normal container surface characteristics, such as threads, seams, seeds, neck rings and blisters. Although they in some respects resemble flaws, they should not cause rejection of the bottle. It is to be understood that although FIG. 2 shows positive peak values, such as would be obtained by light reflection from flaws, the same concepts apply to negative peaks, such as would be obtained from light transmission through flaws. The optical checker of the present invention sets the minimum and maximum durations $T_{min}$ and $T_{max}$ for the optical signal exceeding the threshold $V_T$ to produce a rejection such that $T_{min} < t_2 < T_{max}$ for the known type of flaw but for which $t_1 < T_{min}$ and for which $T_{max} < t_3$. Thereby, both short duration noise and long duration anomalies are passed while the intermediate duration flaws are rejected.

Figure 3:
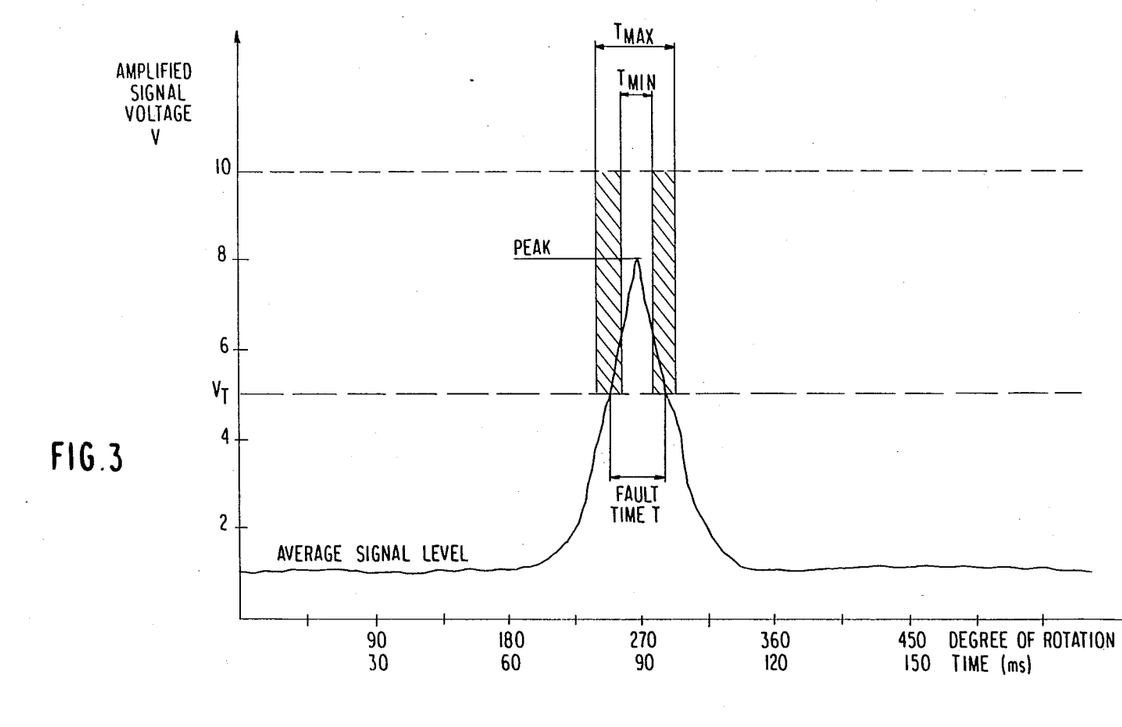
FIG. 3 is a signal vs. time profile for an optical signal from a reference defect bottle.

The invention further provides for automatic setting of all programmable variables, such as gain, threshold, and preset minimum and maximum times. A known defective container is run through the check detector and the computer stores the profile of the signal voltage vs. degree of rotation of the bottle. A typical profile for a reference defect bottle is shown in FIG. 3. After the average signal level has been digitized and stored, the peak value PEAK is determined. In order to keep the electronics operating in narrow range, the gain is adjusted so that the peak value is processed at a set value, for instance, 8 volts. Therefore, the gain setting GAIN is determined by GAIN=$K_3$/PEAK. Then, the threshold $V_T$ is determined as a constant fraction of the peak value PEAK, that is, $V_T = K_0 \cdot \text{PEAK}$. The fault time T is then determined as the duration for which the signal level exceeds the threshold $V_T$. The minimum and maximum durations are then determined as constant fractions of the fault time T, that is $T_{min} = k_1 \cdot T$ and $T_{max} = K_2 \cdot T$. The shaded area of FIG. 3 therefore represents the reject window for the optical bottle checker of the invention.

Typical values for the proportionality constants are $K_0 = 0.63$, $K_1 = 0.7$, $K_2 = 1.4$, and $K_3 = 8$ V.

Figure 4:
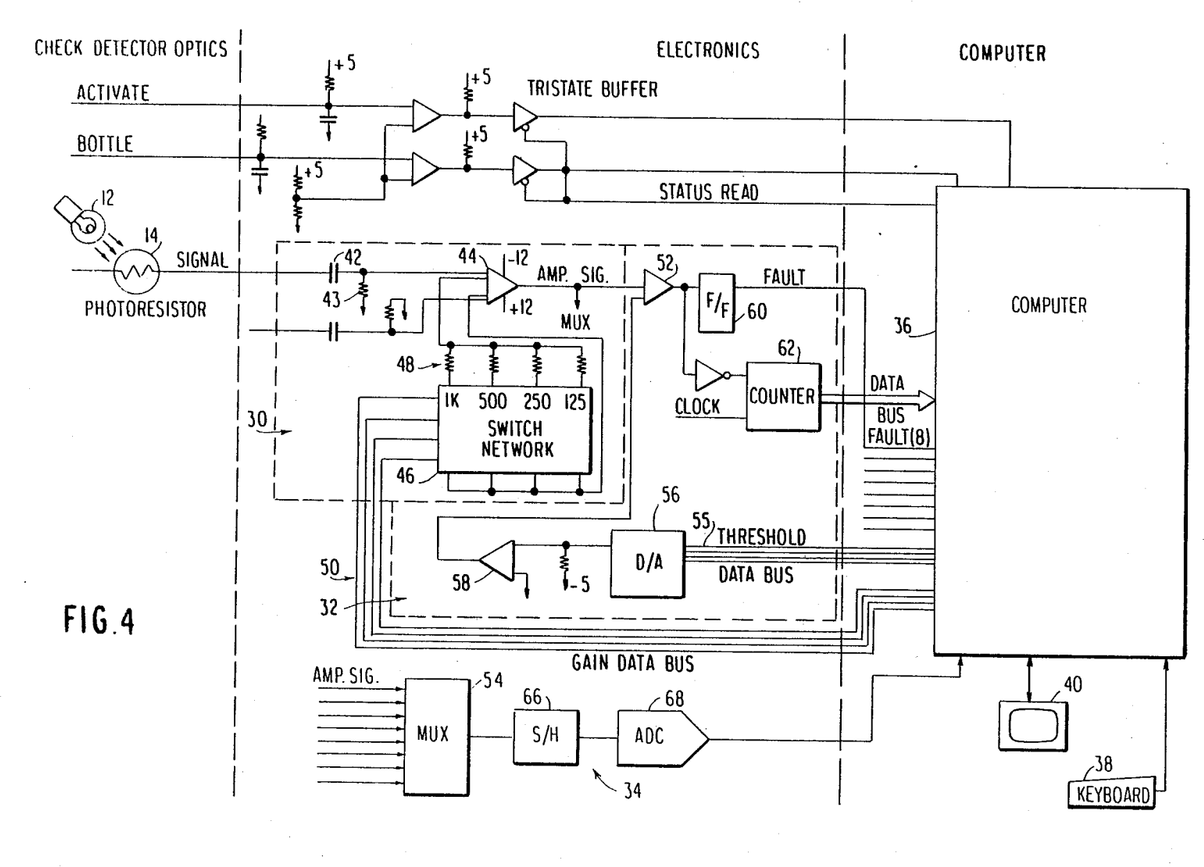
FIG. 4 is a schematic diagram illustrating the electronic hardware for the bottle checker of the invention.

The electronics hardware, beyond that provided by Claypool, which is needed for both the initial setup and the variable threshold testing is illustrated in FIG. 4. It mainly comprises three circuits. A first circuit 30 contains the input signal conditioning and a variable gain amplifier. A second circuit 32 controls the variable threshold and duration timing tests. A third circuit 34 contains the multiplexer and an analog-to-digital converter for signal analysis. These three circuits provide inputs to a computer 36 which performs most of the processing. The computer 36 may be a PC-AT such as that available from IBM Corporation and is controlled by an operator at a keyboard 38 and displays various information on a CRT 40.

In the first circuit 30, the analog signal from the photosensor 14 is received onto an analog board through a connector and is AC coupled through a 0.47 $\mu$F capacitor 42 separated from ground by a 100 k$\Omega$ resistor 43 and then supplied to an instrumentation amplifier 44, such as INA101. The gain of the instrumentation amplifier 44 is controlled by an analog switch network 46, such as an AD7590, having resistors 48 connected in resistances of 125$\Omega$, 250$\Omega$, 500$\Omega$ and 1 k$\Omega$. parallel paths is separately switched by a gain data bus. The gain of the instrumentation amplifier 44 is set by the applied resistance R according to the formula

GAIN=1+40,000/R.

Thus, the gain of the instrumentation amplifier 44 is programmable from 21 to 601 in steps of 40, as shown in the following Table 1.

TABLE 1

| R | GAIN |
|---|---|
| 1000 | 41 |
| 500 | 81 |
| 333 (1K,500) | 121 |
| 250 | 161 |
| 200 (1K,250) | 201 |
| 167 (500,250) | 241 |
| 142 (1K,500,250) | 281 |
| 125 | 321 |
| 111 (1K,125) | 361 |
| 100 (500,125) | 401 |
| 91 (1K,500,125) | 441 |
| 83 (250,125) | 481 |
| 77 (250,125) | 521 |
| 71 (1K,250,125) | 561 |
| 67 (1K,500,250,125) | 601 |

The output of the instrumentation amplifier 44 is supplied both to a voltage comparator 52 in the second circuit 32 and to an eight channel multiplexer switch 54 in the third circuit 36.

In the second circuit 32, the amplified photosensor signal is compared in the comparator 52 against an analog threshold voltage. The comparator 52 may be an LM339. The analog threshold voltage is controlled by a digital threshold data bus 55 controlling an octal D/A converter 56, such as a BT110, and is amplified by an amplifier 58, such as an LM324. Thus, the analog threshold voltage at the input to the comparator 52 can be set between 0 V and +10 V.

From this point, the photosensor signal is processed digitally for display, status and timing. The output of the comparator 52 is used for two functions. First, a flip-flop 60 is set on the rising edge of the fault signal, i.e., when the amplified photosensor signal exceeds the threshold. The output of the flip-flop 60 provides a FAULT status as well as a lit LED display. At this point, it should be mentioned that on one computer card there are eight pairs of first and second circuits 30 and 32 corresponding to eight photosensors 14 positioned around the bottle being inspected. Furthermore, there are two such cards, for a total of sixteen channels. Secondly, the unlatched fault signal is used to enable a counter 62 counting a free running clock signal. The counter 62 may be a 74HC590. The frequency of the clock is 27.965 kHz. which is derived from the system clock of 14.31818 MHz divided by a 74HC294 having a divide factor of 512. In the computer 36, the output of the counter 62 is multiplied by the known clock period of 35.7 μs to obtain the actual time that the photosensor signal is over the threshold. This, of course, would be unnecessary if the time window in FIG. 3 were expressed in terms of numbers of clock cycles. The electrical schematic in FIG. 4 is incomplete in that it shows only a single fault counter 62. As is shown in FIG. 2, there may be more than one peak and the counter value should correspond to the width of a single peak rather than the combined widths of all the peaks. Therefore, it is preferred that there be at least two fault counters 62 per channel. The first one of these would count only a first peak while the second would count all subsequent peaks. Of course, then each fault counter 62 would need to be separately interrogated.

Thus, if during the inspect cycle, a fault is detected (photosensor signal being greater than the threshold). then the flip-flop 62 is set, the LED is turned on and the counter 62 is enabled to count for the duration of the fault signal, that is, the duration of time when the photosensor signal is above the threshold.

In the third circuit 34, the eight channel multiplexer 54 is used to switch one of the eight inputs from the eight instrumentation amplifiers 44 to a sample-and-hold circuit 66 and from there to an A/D converter 68. The sample-and-hold circuit 66 may be an AD582 and the A/D converter 68 may be an AD673. The output of the A/D converter 68 is sampled during the ALIGN phase of the setup to generate the signal bar graph.

To complete the description of the circuitry of FIG. 4, there are two control signals ACTIVATE and BOTTLE. The BOTTLE signal is active (0 V) only during the inspect cycle when a bottle is present to be tested. Otherwise, the BOTTLE signal is inactive (5 V) when there is no bottle during the inspect cycle. Similarly, the ACTIVATE signal goes active (0 V) when the bottle becomes fully rotating, which occurs during an inspect cycle. The ACTIVATE signal changes state to indicate the end of the inspect cycle. It is generated by a cam-actuated proximity switch on the check detector gear box. The computer 36 begins its operation when the ACTIVATE signal goes inactive. The ACTIVATE and BOTTLE signals are buffered by four amplifiers set up in a conventional configuration. The ACTIVATE and BOTTLE signals are each compared to a Reference voltage and then supplied to the input of a tristate buffer. The output of the tristate buffer is supplied to the computer through a data bus.

Figure 5:
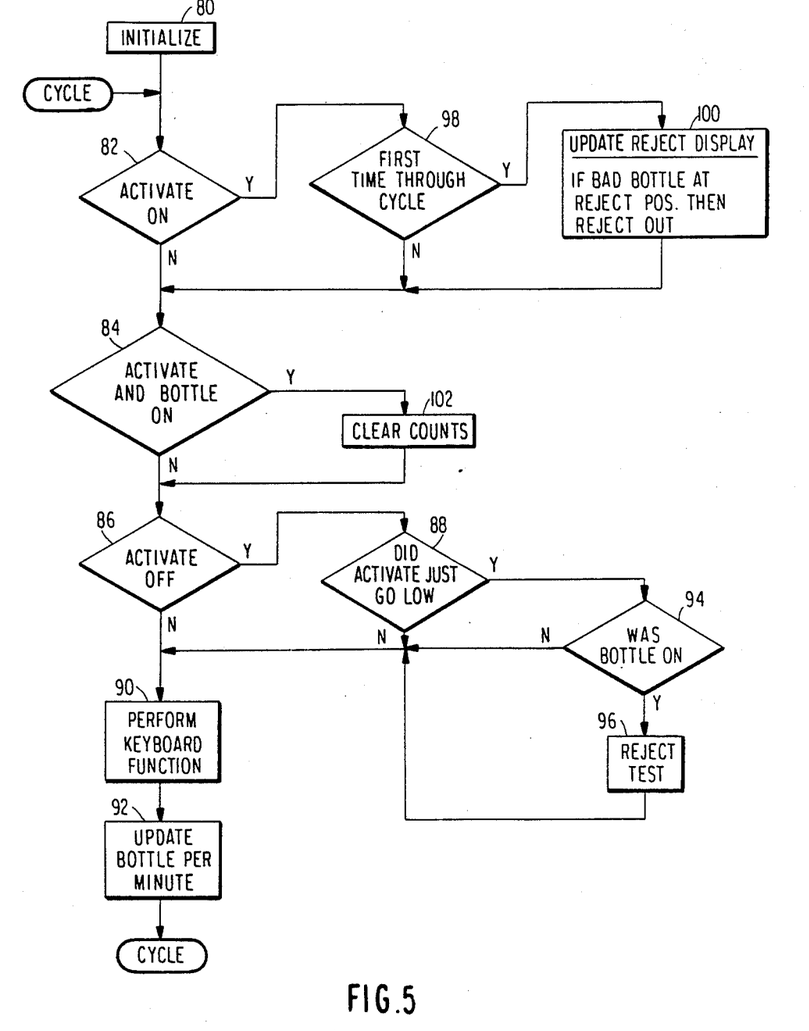
FIGS. 5 and 6 are flow diagrams for the computer software for use with the bottle checker of the invention.
Figure 6:
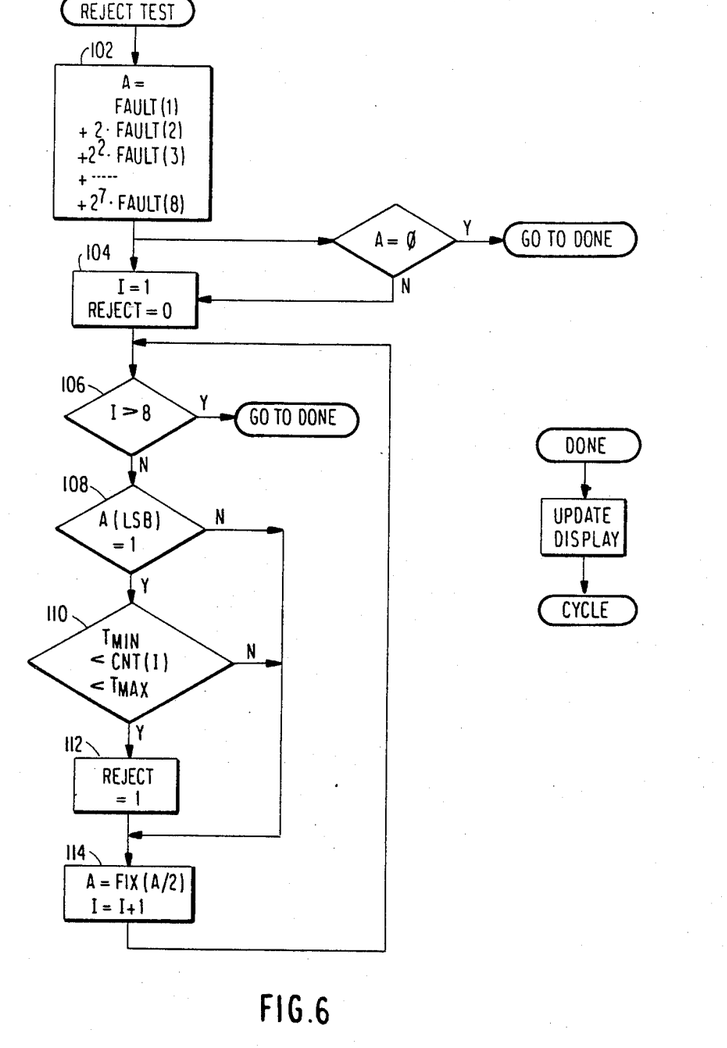

The software to control the computer and its determination of the reject conditions is illustrated in FIGS. 5 and 6. The flow diagram of FIG. 5 involves initialization and the timing of the actual reject determination. After the program is started, in an initial step 80, the parameters for the test are initialized. These parameters are GAIN, the threshold, $V_T$, and the preset times $T_{min}$ and $T_{max}$. This step will be discussed in further detail below. Thereafter, the program operates in a continuous loop. In step 82, it is determined whether the ACTIVATE signal is on (active) If not, then there is no rotating bottle and the program steps through step 84 to step 86 where it is determined that the ACTIVATE signal is inactive. Since the activate signal goes inactive at the end of an inspection cycle, it is determined at step 88 if it has just recently changed to the inactive state. If not, then the program advances to step 90 where any entered keyboard function is performed. Finally, the bottles per minute display is updated in step 92. The program then cycles back to just before step 82.

If in step 88 it was detected that the ACTIVATE signal had just recently gone inactive, it is then determined at step 94 if the BOTTLE signal was active at that time. If so, this signifies the completion of an inspection cycle and the program then enters the REJECT TEST routine 96, which will be described in more detail below.

After the REJECT TEST routine, or if the tests at steps 88 and 94 are negative, the program advances to the housekeeping steps 90 and 92 as described above.

If at step 82 it is determined that the ACTIVATE signal is active, the system then checks at step 98 to see if this is the first time through the testing cycle. If so, then the program advances to step 100 where it is determined if the bottle at the REJECT position is a bad bottle as determined from the previous REJECT TEST, and if so it is cleared out and the reject indication is cleared.

If this is not the first time through the cycle, then a test may be in progress and the program simply advances through step 98 to step 84. In this scenario, the ACTIVATE signal has been found at step 82 to be active, and at step 84 it is then determined whether the BOTTLE signal is also active indicating that a test is ready to be run. If so, the fault counters are cleared at step 102, and the system will proceed through steps 86, 90, 92, 82, 98, 84 and 102 until the end of the inspection cycle is detected at step 86. The REJECT TEST is then performed at step 96 in accordance with the inspection data collected.

The REJECT TEST routine 96 is illustrated in FIG. 6. In step 102, the software uses the fault signals FAULT(I) from the first eight channels to create an 8-bit fault digit A. This fault digit may be simply derived by connecting the respective lines carrying the separate fault signals to the proper lines of an 8-bit bus in the computer 36. If no faults have been detected, A=0 and the REJECT TEST routine is exited after appropriate display update. If there is at least one fault in the fault vector, then in step 104 a counter I is set to one and the REJECT condition is set to zero. A test 106 determines if all eight channels have been tested. If so, the test cycle is completed and processing returns to FIG. 5. However, if there is a second set of eight channels of photosensor data, then this data is provided to step 102 for calculation of another 8-bit fault digit A and for subsequent processing of the data.

Each non-zero bit of the fault digit A indicates that the threshold has been exceeded for that channel. In test 108, the least significant bit of the fault digit A is compared to 1. If the bit is 1, in test 110 it is determined whether the fault count CNT(I) for the I-th channel is within the duration window defined by $T_{min}$ and $T_{max}$. If so, the REJECT condition is set to one in step 112. If either of the tests 108 and 110 produces a negative result, the REJECT condition is not changed. In any case, in step 114 the fault digit A is divided by two and truncated and the count I is incremented so that a new channel is tested in the subsequent execution of the loop.

One of the advantages of a fully computerized checker electronics 18 is the ability to automate the setup procedure for different types of bottles. The software for automatic setup is illustrated in the flow diagram of FIG. 7. In a first step, a standard bottle with a standard flaw is rotated ten times and a selected sensor has its signal selected by the multiplexer 54 and the entire scan for each rotation is digitized by the A/D converter 68. The computer 36 determines the peak value for each scan and sets a variable $S_i$ to this peak value. Ten such values are found. In step 142, the average peak value PEAK is determined from the $S_i$. In test 144, the presently set value of GAIN in the switch network 46 is compared to a maximum value $GAIN_{max}$, for instance, $GAIN_{max}=601$ in the table. Initially GAIN is set to a value less than $GAIN_{max}$. If the GAIN has not yet been increased to $GAIN_{max}$, then test 146 determines if the last measured value PEAK is 8 V or within a small range thereof. The purpose of the first loop in the auto setup is to adjust GAIN until PEAK=8 V. If the maximum gain has been reached or the peak value is 8 V, the loop is left. Otherwise, the GAIN is incremented or decremented in step 148 depending on whether PEAK is below or above 8 V, and the standard bottle is again checked with the new value of GAIN.

Figure 7:
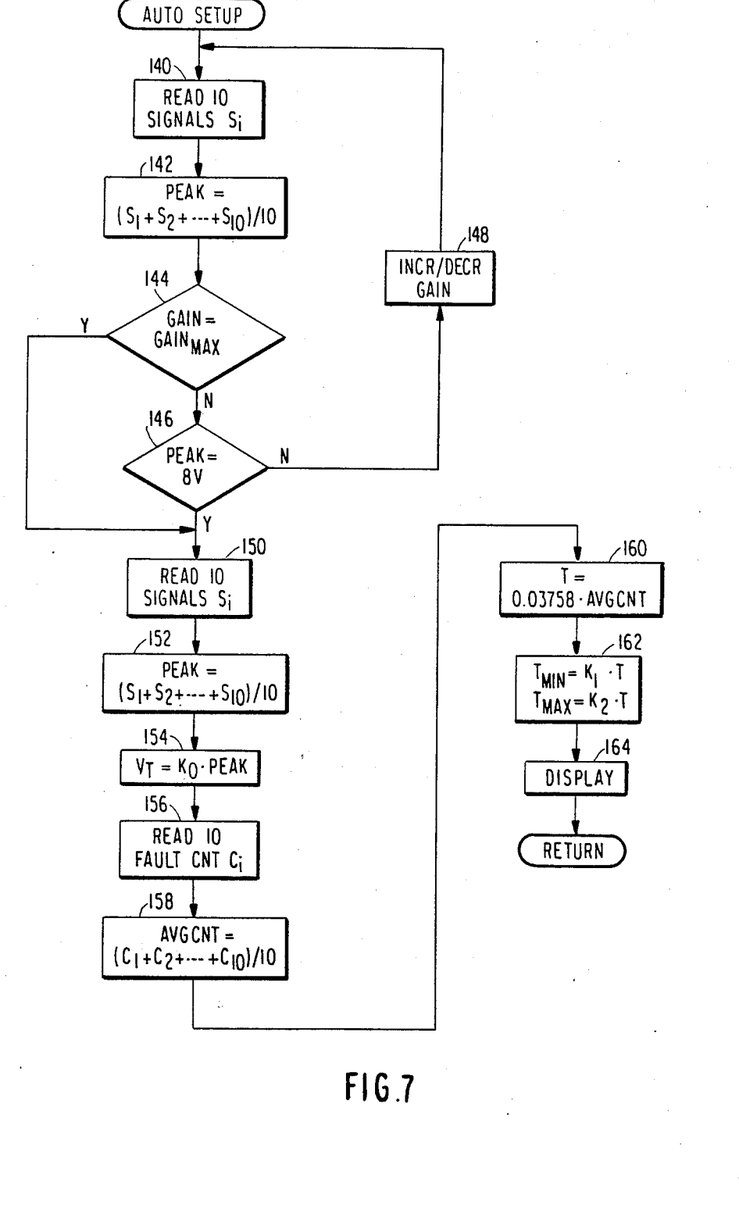
FIG. 7 is a flow diagram for the automatic setup of the parameters for bottle checking.

Upon exiting the gain setting loop, in steps 150 and 152 (similar to steps 140 and 142). a new PEAK value is determined. Then in step 154, a threshold $V_T$ is determined as a constant fraction $K_0$ of PEAK, i.e., $V_T = K_0 \cdot PEAK$. Then, with this threshold value $V_T$ applied to the D/A converter 56, the standard bottle is again rotated ten times to obtain in step 156 ten values of the FAULT CNT $C_i$ from the fault counter 62. In step 158, these ten values of $C_i$ are averaged to obtain an average fault count AVGCNT. In step 160, the average fault count is multiplied by a clock constant to obtain the average time width T in milliseconds of the peak. In step 162, the time width T is multiplied by constants $K_1$ and $K_2$ to obtain respectively the minimum and maximum time windows $T_{min}$ and $T_{max}$. The results of the auto setup are then displayed in step 164.

Figure 8:
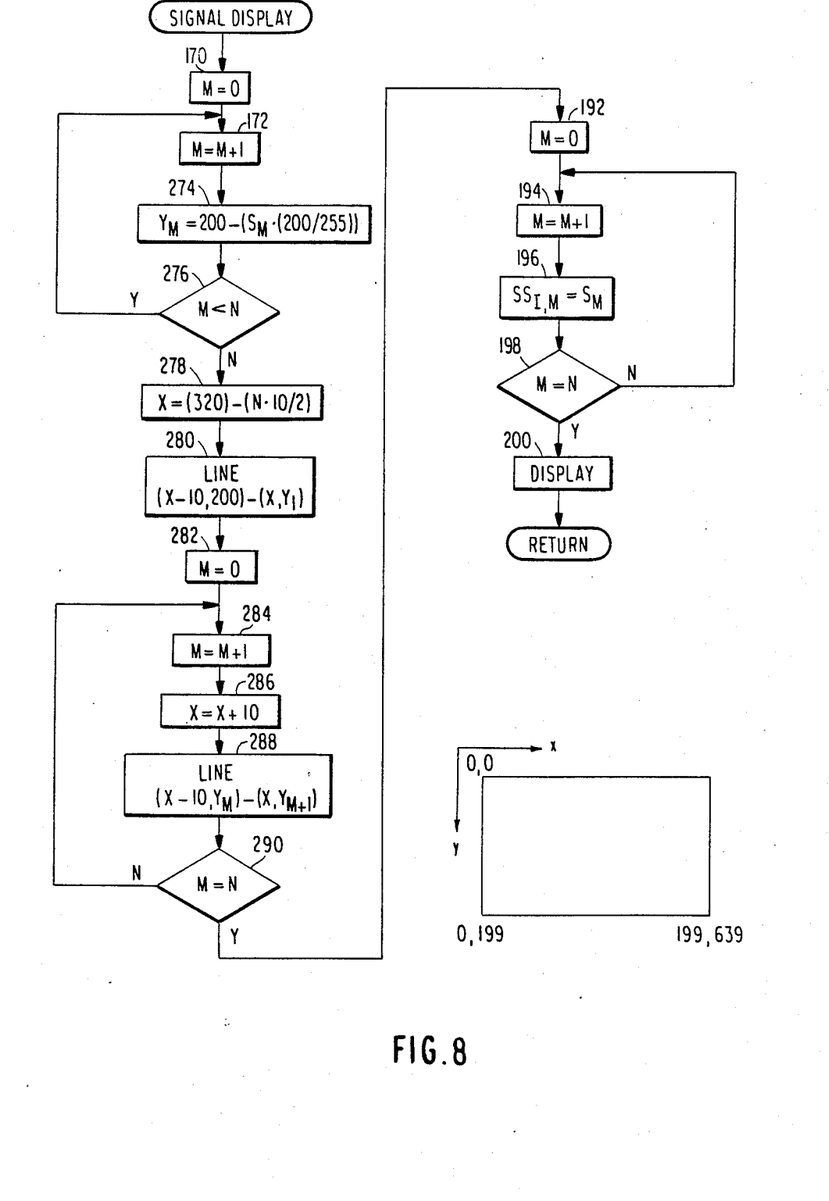
FIG. 8 is a flow diagram for the display of a complete bottle checking scan.

The details of the display procedure are shown in the flow diagram of FIG. 8. The display is performed on a CGA video display having a resolution of $200 \times 640$ dots. An index $\overline{M0}$ is initialized in step 170 and then incremented inside a loop in step 172. The sampled data $S_M$ is digitized in 8 bits so that it has a maximum value of 255 and is then normalized to displayed data $Y_M$ with 200 dot vertical range in step 274, that is, $Y_M = 200 - (S_M \cdot (200/255))$. A test 276 for M<N determines whether all the N sampled data have been normalized. A typical value for N is 60.

In the horizontal direction, there are 640 dots in the displayable range. Each of the N sampled data will be displayed 10 dots apart and will be centered about the horizontal center of the screen. A starting point $X = (320) - (N \cdot 10/2)$ is determined in step 278. In step 280, a line is drawn between the bottom of the screen at one increment before the starting point to the starting point with the first normalized sampled value $Y_1$. An index M is initialized to zero in step 282. Inside a loop, the index $\overline{M0}$ is incremented in step 284 and the X value is increased by 10 in step 286 for the next sampled data. In step 290, a line is drawn between the points for $Y_M$ and $Y_{M+1}$. The loop is repeated until test 290 determines that M=N.

There are multiple channels of data available in the bottle checker. In the following steps, the sampled data $S_M$ are stored in a multi-dimensional array $SS_{I,M}$ for possible later retrieval. In this process, the index M is initialized in step 192 and is incremented inside the loop in step 194. The sampled data $S_M$ is then transferred to the I-th subarray in $SS_{I,M}$ in step 196. A test 198 determines if all N sampled values have been so transferred. In step 200, all generated lines are displayed.

Figure 9:
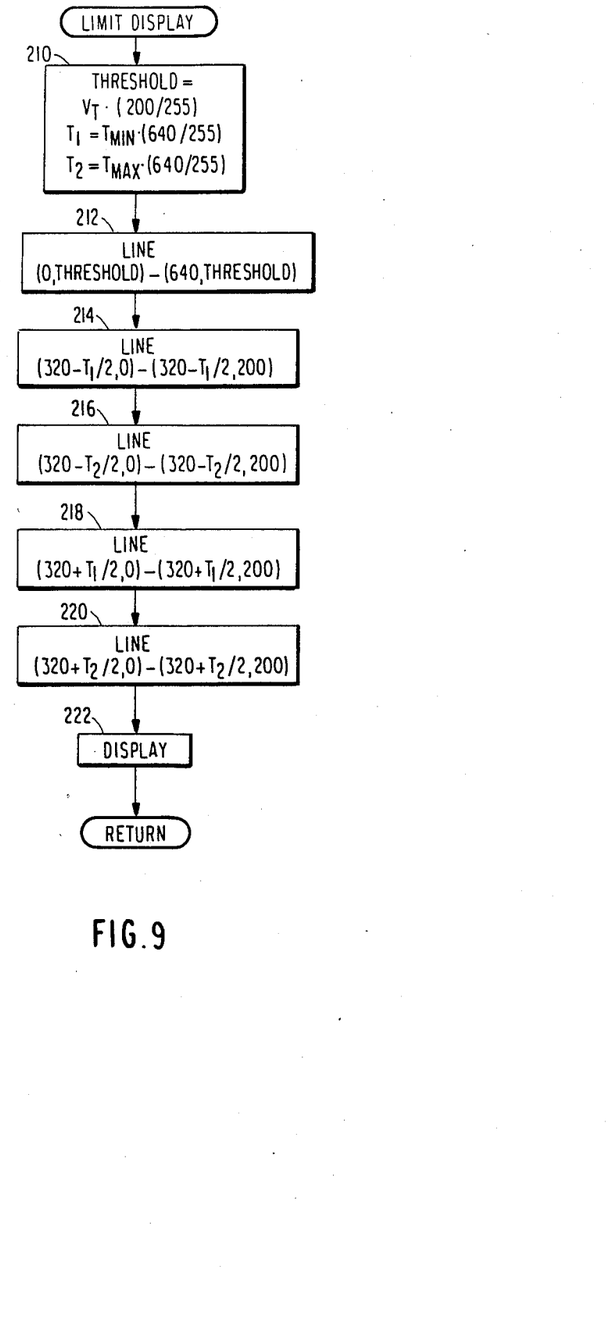
FIG. 9 is a flow diagram for the display of the limits used in the bottle checking.

In order to facilitate the understanding of the display, additional lines can be added to the display described above which indicate the limits imposed by the automatic setup. As shown by the flow diagram of FIG. 9, in step 216 the threshold voltage $V_T$ and the minimum and maximum window times $T_{min}$ and $T_{max}$ are converted to normalized values THRESHOLD, $T_1$ and $T_2$. In step 212, a line is drawn from the left to the right of the screen at the THRESHOLD value. In step 214, a line is drawn for the left $T_{min}$ limit. In step 216, a line is drawn for the left $T_{max}$ limit. Similar lines are drawn in steps 218 and 220 for the right $T_{min}$ and $T_{max}$ limits. All of the limit lines are drawn from the bottom to the top of the screen and are centered horizontally about the center of the screen. Of course, the measured peak having a duration above the threshold for the time duration window between $T_{min}$ and $T_{max}$ does not need to occur at the center. Finally, in step 222 all the so generated limit lines are displayed on the screen.

The check detector is run under computer control so that all operations are controlled by the operator keying in appropriate instructions at the computer terminal. The HELP screen menu for entry into various control routines is shown in Table 2.

TABLE 2

| BMS CHECK DETECTOR HELP SCREEN | |
|---|---|
| KEY | FUNCTION |
| F1 | DISPLAY THIS SCREEN |
| F2 | ALTERNATE PAGE 1 AND 2 |
| A | AUTOMATIC SETUP |
| F3 | ALIGNMENT AND SENSORS |
| F4 | ADJUST SENSOR |
| R | RESTART PROGRAM |
| S | STOP PROGRAM |
| C | CLEAR ALL COUNTERS |
| P | PUT SETUP ON DISK |
| G | GET SETUP FROM DISK |
| WITH PAGE 1 OR PAGE 2 DISPLAYED. DEPRESS F5 TO ADJUST ANY SENSOR. USE CURSOR KEYS TO SELECT ITEM THEN + OR − TO ADJUST VALUE UP OR DOWN. AFTER ALL SENSORS ARE SETUP, USE P TO SAVE ALL VALUES AND G TO RESTORE. | |

The automatic setup has already been described. Once this automatic setup has been performed, the setup parameters can be saved on disk for later retrieval of any one set of parameters without the necessity of using the standard bottle to repeat the automatic setup. The menu for the G command allows the selection of a set of parameters.

Whenever there is a keyboard function performed, the computer automatically stores the present values of all variables (gain, threshold, maximum and minimum time values for each channel). Thus, in the event of a malfunction, e.g., loss of power. etc., it is not necessary to repeat the automatic set-up or to re-enter the data.

Figure 10:
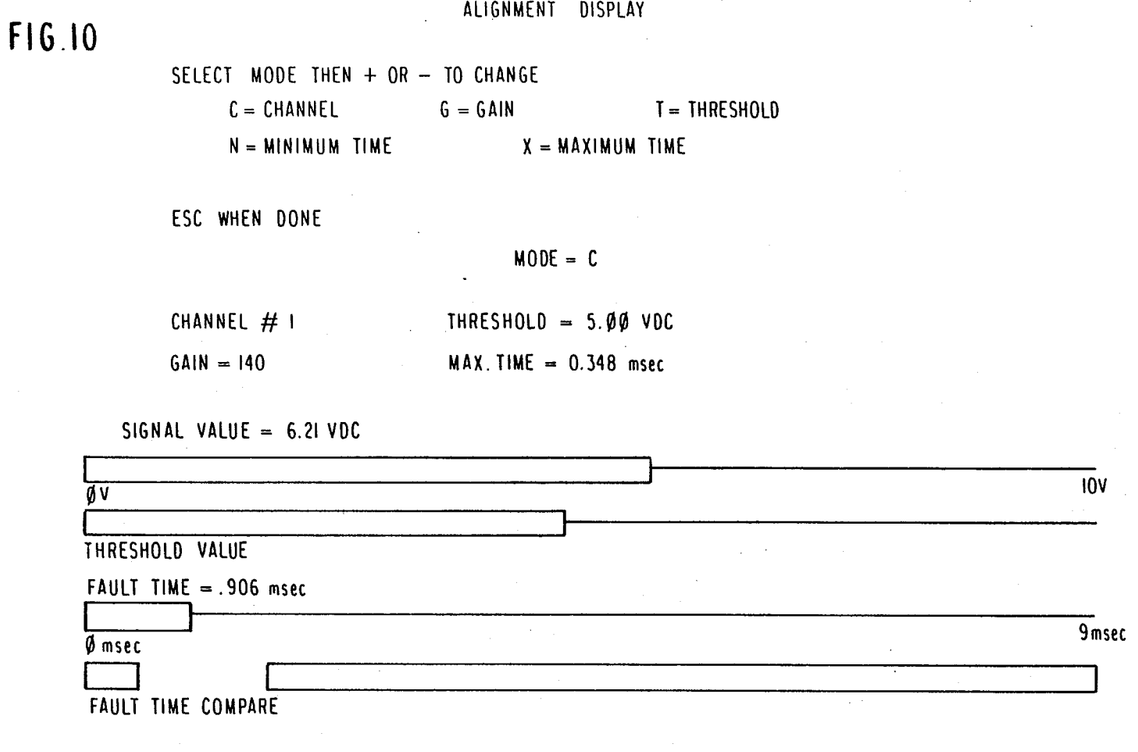
FIG. 10 is an alignment display for manual setting of bottle checking parameters.

Rather than using the automatic setup, it is possible to manually adjust the sensor gain by use of the ADJUST SENSOR selection, which causes the display of the screen shown in FIG. 10. With this alignment menu, keying in + or − causes the gain to be incremented or decremented.

During normal running operation of the bottle checker, the screen may be set either for the alignment display of FIG. 10 for one of the channels or for the the main display of the results of all of the channels of fault checking as shown in the following Table 3.

TABLE 3

| TOTAL BOTTLES | BPM | TOTAL FAILURES |
|---|---|---|
| 0 | 0 | 0 |

| CHAN. | FAULTS | GAIN | LEVEL | MIN-TIME | MAX-TIME |
|---|---|---|---|---|---|
| 1 | 0 | 140 | 5.00V | 0.348MS | 1.500MS |
| 2 | 0 | 140 | 5.00V | 0.348MS | 1.500MS |
| 3 | 0 | 300 | 6.25V | 0.196MS | 0.450MS |
| 4 | 0 | 300 | 6.25V | 0.196MS | 0.450MS |
| 5 | 0 | 240 | 5.00V | 0.280MS | 0.560MS |
| 6 | 0 | 140 | 4.00V | 0.450MS | 0.950MS |
| 7 | 0 | 140 | 4.00V | 0.450MS | 0.950MS |
| 8 | 0 | 140 | 4.00V | 0.450MS | 0.950MS |
| 9 | 0 | 240 | 5.00V | 0.320MS | 0.600MS |
| 10 | 0 | 300 | 5.00V | 0.320MS | 0.600MS |
| 11 | 0 | 300 | 5.00V | 0.320MS | 0.600MS |
| 12 | 0 | 280 | 5.50V | 0.300MS | 0.600MS |
| 13 | 0 | 140 | 4.00V | 0.450MS | 0.950MS |
| 14 | 0 | 140 | 4.00V | 0.450MS | 0.950MS |
| 15 | 0 | 140 | 4.00V | 0.450MS | 0.950MS |
| 16 | 0 | 140 | 4.00V | 0.450MS | 0.950MS |

INSPECTION STATION 0000   DELAY 4
DEPRESS F1 KEY FOR HELP

In the above table, BPM represents bottles per minute, that is, the operation rate of the bottle checker. The parameter DELAY represents how many bottle positions there are between the position at which the bottles are checked and the position at which rejected bottles are kicked from the testing line.

Thus, it is possible to adjust any of the set-up parameters manually through either the ADJUST SENSOR selection (with the display shown in Table 3) or the ALIGNMENT selection (with the display shown in FIG. 10). Using the ADJUST SENSOR selection, the cursor is moved to the desired variable, and the new value is entered. The ADJUST SENSOR selection may be used when the check detector is running. Using the ALIGNMENT selection, the mode (i.e., the variable desired) is selected by entering on the keypad the appropriate letter. Then, the value of the variable selected is changed by keying in "+" or "−" to increment or decrement.

What is claimed is:

1. A testing apparatus for checking defects in an article, comprising:
   a source of radiation for irradiating an article;
   means for moving said article at a predetermined velocity relative to said radiation source:
   at least one photosensor for receiving light which was emitted from said radiation source and which has interacted with said moving article;
   a variable gain amplifier receiving an output of said photosensor;
   a comparator for comparing an output of said variable gain amplifier with a threshold value and thereby producing a comparator output:
   a clocked counting circuit receiving an output of said comparator for counting a time said comparator produces a predetermined value of said comparator output; and
   first means for determining when said counting circuit has counted a value falling between a preset minimum value and a preset maximum value, said determining means thereby providing a reject signal for said article.

2. A testing apparatus as recited in claim 1, wherein said article is a bottle and wherein said moving means rotates said bottle through a complete circle.

3. A testing apparatus as recited in claim 2, further comprising:
   means for finding a peak value of an output of said variable gain amplifier for a series of values produced during a rotation of a standard bottle; and
   means for calculating said threshold value from said peak value.

4. A testing apparatus as recited in claim 3, further comprising:
   means for determining a standard count value of said counting circuit during a rotation of said standard bottle; and
   means for determining said preset minimum value and said preset maximum value from said standard count value.

5. A testing apparatus as recited in claim 4, further comprising:
   means for storing on a magnetic disk storage medium said threshold value and said preset minimum and maximum values; and
   means for retrieving from said storage medium said threshold value and said preset minimum and maximum values for an operation of said counting circuit and said first determining means.

6. A testing apparatus as recited in claim 1, further comprising means to adjust a gain of said variable gain amplifier so that a peak value of said variable gain amplifier falls within a predetermined range when said moving means moves a standard bottle.

7. A testing apparatus as recited in claim 1, further comprising means for varying any of said preset minimum and maximum values and said threshold value.

8. A testing apparatus as recited in claim 7, further including means for graphically displaying in real time said photosensor output, said threshold value, a fault time corresponding to said counted value and a time window defined by said preset minimum and preset maximum values.

9. A testing apparatus as recited in claim 1, wherein said comparator performs a real time analog comparison.

10. A testing apparatus as recited in claim 3, further comprising means for displaying the output of said variable gain amplifier to graphically show the peak value produced during a rotation of said standard bottle.

11. A testing apparatus as recited in claim 4, further comprising means for displaying the threshold value, preset minimum value and preset maximum value.

12. A testing apparatus as recited in claim 5, further comprising means for automatically storing said threshold value, said preset minimum and maximum values and the gain of said amplifier after any change or entry of said values.

13. A testing apparatus as recited in claim 9, further comprising means for displaying the threshold value, preset minimum value and preset maximum value.

14. A testing apparatus for checking defects in an article, comprising:
   a source of radiation for irradiating an article;
   means for moving said article at a predetermined velocity relative to said radiation source;

at least one photosensor for receiving light which was emitted from said radiation source and which has interacted with said moving article;

a variable gain amplifier receiving an output of said photosensor;

a comparator for comparing an output of said variable gain amplifier with a threshold value and thereby producing a comparator output;

a clocked counting circuit receiving an output of said comparator for counting a time said comparator produces a predetermined value of said comparator output;

first means for determining when said counting circuit has counted a value falling within a preset range, said determining means thereby providing a reject signal for said article; and means to adjust a gain of said variable gain amplifier so that a peak value of said variable gain amplifier falls within a predetermined range when said moving means moves a standard bottle.

15. A testing apparatus as recited in claim 14, further comprising:

means for storing a plurality of sets of parameters defining said threshold value, said preset range and said predetermined range of said gain of said variable gain amplifier; and means for retrieving any selected ones of said plurality of sets for use by said variable gain amplifier, said comparator and said first determining means.

* * * * *